United States Patent [19]

Rei et al.

[11] 4,086,297
[45] Apr. 25, 1978

[54] METHOD OF MAKING POLYMERIC COMPOSITIONS AND COMPOSITIONS THEREFOR

[75] Inventors: Nuno M. Rei, Peabody; Nicholas J. Hill, Andover, both of Mass.

[73] Assignee: Ventron Corporation, Beverly, Mass.

[21] Appl. No.: 736,968

[22] Filed: Oct. 29, 1976

Related U.S. Application Data

[63] Continuation-in-part of Ser. No. 635,755, Nov. 28, 1975, abandoned.

[51] Int. Cl.² .................... C08K 5/43; C08K 5/39; C08K 5/34; C08K 5/53
[52] U.S. Cl. ............... 260/859 PV; 260/45.8 N; 260/45.75 K; 260/45.75 B; 260/45.95 H; 260/897 C; 260/899
[58] Field of Search ................ 260/45.8 N, 45.75 B, 260/45.75 K, 859 PV, 897 C, 899; 106/15 AF; 424/78–83

[56] References Cited

U.S. PATENT DOCUMENTS

| | | | |
|---|---|---|---|
| 3,257,351 | 6/1966 | Kraus et al. | 260/41 |
| 3,415,832 | 12/1968 | Crawford | 260/294.8 F |
| 3,658,994 | 1/1972 | Domenico | 260/294.8 F |
| 3,755,244 | 8/1973 | Hart | 260/41 |
| 3,758,482 | 9/1973 | Domenico | 260/294.8 F |

OTHER PUBLICATIONS

Stabilization of Polymers and Polymer Processes – A. C. Society – 1968, pp. 250 to 271.
SPE Journal – 1970, vol. 26, pp. 26 to 30.

*Primary Examiner*—V.P. Hoke
*Attorney, Agent, or Firm*—Paul J. Cook

[57] ABSTRACT

A solid composition comprising a homogeneous mixture of a solid thermoplastic resin and from 1 to 80 weight % of at least one microbiocide which is insoluble in water, is readily dispersible or soluble in the resin at temperatures sufficiently high to permit plastic manipulation of the resin and the dispersion or solution of the microbiocide is sustained indefinitely upon cooling to ambient temperature while the diffusivity of the microbiocide in the resin under such conditions becomes vanishingly small, retains its microbiocidal activity in the resin and does not degrade or react with the resin in which it is dispersed. This compositon provides a convenient non-toxic dosage form of the microbiocide which is subsequently mixed with a second thermoplastic resin at a concentration of about 0.5 to 15 weight % to obtain a homogeneous resin composition containing an effective amount of the microbiocide.

42 Claims, No Drawings

METHOD OF MAKING POLYMERIC COMPOSITIONS AND COMPOSITIONS THEREFOR

BACKGROUND OF THE INVENTION

This application is a continuation-in-part of application Ser. No. 635,755, filed Nov. 28, 1975 now abandoned.

This invention relates to solid resin-microbiocide compositions and to a method for forming resin products therewith. More particularly, the present invention relates to solid polymeric compositions containing a high concentration of a microbiocide for the purpose of providing an easily handleable, predispersed and a relatively non-toxic form of the biocide and a method for forming resin resin products therefrom.

Resin compositions are protected against fungal or bacterial attack by incorporating a microbiocide therein to prevent the deterioration of articles formed from the resin composition due to microbiological attack on the susceptible portion of the components of the resin system. In order for the microbiocide to be effective in the resin composition, it is necessary that it be compatible therewith and uniformly dispersible in the resin composition to avoid forming resin composition portions free of the microbiocide which would be susceptible to attack. Heretofore, microbiocide compositions have been added to resins either as a powder or as a liquid composition. To assure compatibility and adequate dispersibility of the microbiocide, it was believed necessary to add the microbiocide with a liquid carrier such as a plasticizer for the resin thereby providing a vehicle for the microbiocide to promote its migration throughout the resin, particularly to its surface. The presently employed procedures usually involve first mixing the microbiocide in a liquid carrier which solubilizes of disperses the microbiocide uniformly followed by mixing the liquid composition with the final resin composition. The liquid solvents or dispersants employed are those which do not degrade the properties of the final resin product such as plasticizers when employed at moderate concentrations. Unfortunately, the solubility of many of the commonly used microbiocides in common liquid resin additives is quite low. Therefore, it is difficult to incorporate a sufficiently high concentration of the microbiocide with the resin while avoiding an undesirably high concentration of the liquid carrier. Also, this procedure imposes restrictions on the choice of plasticizer to be used in the final resin composition. In addition, it is desirable to avoid using plasticizers with some thermoplastic resins such as polyurethanes.

Alternatively, it has been proposed to add the microbiocide directly to a formable resin compositon at the low effective concentrations which prevents microbiological attack. However this procedure has proven to be unsatisfactory since the needed concentrations of microbiocide is quite low, generally less than about 1 weight % and usually between about 200 and 1000 parts per million. If the microbiocide were to be employed in the resin at higher concentrations, the toxicity of the final product made therefrom may be dangerously increased. Therefore, if this procedure is employed, the processor must continuously carefully weigh small amounts of microbiocides to be added to the final product. Since most microbiocides available for protecting resins are powders, continuous handling of a fine-powdered solid which can easily be dispersed in air presents a major toxicological problem to the personnel working in the immediate area. To eliminate these toxicological problems, major changes would be required in presently employed commercial plastic processing techniques which would render them expensive and commercially unfeasible. For this reason, the commercial processor utilizes the microbiocide in a liquid carrier which is somewhat less innocuous than the microbiocide per se. In addition, in order to attain homogeneous dispersion of these low concentrations of microbiocide into the resin, it is necessary to extend the mixing time of the resultant composition. Furthermore, mixing of these resin compositions containing low concentrations of microbiocides results in the microbiocide being coated on the surface of the mixing apparatus rather than being homogeneously dispersed throughout the resin.

It would be highly desirable to provide solid microbiocidal compositions having high concentrations of a microbiocide, above its usually employed effective concentrations, which eliminates the need for a liquid carrier. This would permit incorporating the microbiocide at the desired concentration subsequently into a resin composition while avoiding toxicological hazards and while providing improved control of the concentration of liquid additives in the final resin product. Furthermore, it would be desirable to provide such compositions wherein the microbiocide does not degrade the resin and is not itself degraded when incorporated in the resin so that the composition can be incorporated subsequently into a resin wherein the microbiocide is present at effective concentrations.

SUMMARY OF THE INVENTION

This invention provides solid compositions comprising a thermoplastic resin containing between about 1 and 80 weight % of at least one microbiocide which is insoluble in water, is readily dispersible or soluble in the resin at temperatures sufficiently high to permit plastic manipulation of the resin and the dispersion or solution of the microbiocide is sustained indefinitely upon cooling to ambient temperature while the diffusivity of the microbiocide in the resin under such conditions becomes vanishingly small, retains its microbiocidal activity in the resin and does not degrade or react with the resin in which it is dispersed. Representative suitable microbiocides include 10, 10'-oxybisphenoxarsine, N-(trichloromethylthio)-4-cyclo-hexene-1,2-dicarboximide, 2,3,5,6-tetrachloro-4-(methylsulfonyl) pyridine and N-(trichloromethylthio) phthalimide which is dispersed and/or solubilized in the resin. The solid compositions are both compatible and homogeneously dispersible in a second thermoplastic resin composition to provide effective resistance against microbiocidal attack on the second thermoplastic resin composition. The solid microbiocidal compositions are prepared by mixing the microbiocide and resin under conditions such that the microbiocide is rendered substantially nonmigratory to form a homogeneous composition. These microbiocides also function as processing aids for the resin in that they reduce the processing temperatures needed to form homogeneous compositions. Even though the concentration of the microbiocide is above that which would normally present a toxicological hazard, the homogeneous microbiocide-resin composition is far less toxic than either the microbiocide itself or liquid compositions containing the microbiocide. These compositions can be made without employing a liquid carrier for the microbiocide so that unwanted liquid additives in the second resin composition to be fabricated can be avoided. The concentrated microbiocide-resin composition is incorporated into the second resin composition in amounts such that the two compositions are compatible and such that the final resin composition contains the microbiocide at an effective concentration and below the concentration that presents a toxicological hazard.

DESCRIPTION OF SPECIFIC EMBODIMENTS

The compositions of this invention contain the microbiocide at a concentration which permits the subsequent incorporation of the resultant composition into a second thermoplastic resin composition as a concentration between about 0.5 and 15 weight % based upon the total weight of the resultant composition. When less than about 0.5 weight % of the composition of this invention is incorporated into the second thermoplastic resin composition, less than homogenous dispersion may be obtained which causes the resultant composition to have underprotected areas. When more than about 15 weight % of the composition of this invention is incorporated into a second thermoplastic resin which is different than the first thermoplastic resin, the two resins may become incompatible. In addition, when more than about 15 weight % of the composition of this invention is incorporated into a second thermoplastic resin different from the first thermoplastic resin, undesirable changes in the physical characteristics of the second thermoplastic resin occurs in that they approach those of the first thermoplastic resin.

The concentration of microbiocide in the composition of this invention is between about 1 and 80 weight %, preferably from about 5 to about 55 weight %, based upon the total weight of the thermoplastic composition. The microbiocide concentration depends upon the particular microbiocide and composition and its relative compatibility in the resin. In each instance, the microbiocide concentration is at least about 20 times greater than its normal upper usage concentration in the final resin composition. For example, 10,10'-oxybisphenoxarsine is used normally in a concentration up to 0.05 weight %, N-(trichloromethylthio)-4-cyclo-hexene-1,2-dicarboximide is used normally in a concentration up to 0.5 weight %; 2,3,4,6-tetrachloro-4-(methylsulfonyl) pyridine is used normally in a concentration up to 0.75 weight %; N-(trichloromethylthio) phthalamide is used normally in a concentration up to 0.75 weight % or Zinc Omadine or tributyl tin fluoride wich are used normally in a concentration up to 0.2 weight %. In any event, the microbiocide concentration is controlled so it is present in an effective concentration in a second thermoplastic resin composition when added thereto between about 0.5 and 15 weight % based upon the weight of the second thermoplastic resin composition.

In order to form homogeneous resin-microbiocide compositions, the microbiocide is readily dispersible or soluble in the resin at temperatures sufficiently high to permit plastic manipulation of the resin and the dispersion or solution of the microbiocide is sustained indefinitely upon cooling to ambient temperature while the diffusivity of the microbiocide in the resin under such conditions becomes vanishingly small at the high microbiocidal concentrations utilized herein. In addition, the microbiocide must retain its activity and not itself become degraded or does not degrade the resin either during mixing with the resin or after being incorporated into the resin. Stablity of the microbiocide-resin concentrate is determined readily by visual observation wherein irreversible dark coloring of the concentrate represents degradation of the composition so that it is not useful in the present invention. For example, the microbiocide, ortho-benzyl parachlorophenol is miscible in resins, particularly vinyl resins but the resultant resin-microbiocide composition turns irreversibly black and therefore is not useful herein. Tributyl tin oxide is another common microbiocide not useful herein since it is essentially immiscible with vinyl resins. It is also essential that the microbiocide be substantially insoluble in water so that it is not easily leached from the resin-microbiocide composition either during normal storage or normal use.

The degree of retention of microbiocidal activity in the resin-microbiocide concentrate is determined in any conventional manner wherein the concentrate is incorporated into a plasticized second resin to obtain a composition containing the normal upper range concentration of the microbiocide. This composition then is placed in a petri dish, innoculated with a microorganism against which the microbiocide is normally effective and the zone of inhibition is observed in a conventional manner.

Since the microbiocide is far less migratory within the resin than the microbiocide per se or the microbiocide in solution, it is far less toxic than the microbiocide per se or liquid solutions of the microbiocide even though present at higher concentrations than its effective concentration. Accordingly, it can be incorporated subsequently in a second thermoplastic resin composition with reduced hazard to working personnel since the dusting problem associated with the powdered microbiocides is eliminated. Furthermore, the composition of this invention reduces contamination of processing and weighing equipment and facilitates clean-up of this equipment.

The compositions of this invention normally have poor end use physical properties. Therefore, they must be incorporated into another thermoplastic resin to produce useful fabricated thermoplastic products. However, due to their less toxic nature, the composition of this invention provides a significant advantage over the prior art compositions in that they can be processed safely in conventional thermoplastic resin fabrication techniques without requiring costly safety equipment and without the need for a liquid carrier for the microbiocide.

In another aspect of this invention, it has been found that the microbiocides employed herein, when employed in high concentrations, function as processing aids in that they reduce the melt viscosity and softening point of the thermoplastic resin to such a degree that the resin and microbiocide composition can be processed to form a homogeneous composition without the need for plasticizers for the resin. That is, the microbiocide has the effect of reducing the viscosity of the thermoplastic resin so that when the two are mixed, such as by milling, the resultant composition can be heated to temperatures normally employed in resin-forming processes without the need for adding proccessing aids that reduce the viscosity of the resin or which provide heat stability to the resin. This is surrising since this effect on the resin is not observed when the microbiocide is incorporated at the normally low concentrations at which the microbiocide is effective to prevent or to inhibit microbiological attack without presenting a toxicological hazard to humans. The degree of this effect is dependent upon the type of thermoplastic resin employed, the type of microbiocide employed and the concentration of microbiocide employed.

The compositions of this invention are prepared by mixing a particulate thermoplastic resin with a high concentration of microbiocide such that a homogeneous composition can be obtained without the need for additional processing aids such as a plasticizer, a heat stabilizer or a lubricant for the resin to obtain the advantages set forth above. However, they can be added if desired for special effect. The microbiocide and resin are mixed to obtain a dry homogeneous particulate composition. Thereafter, the composition is heated and mixed so that the resin is melted to a homogeneous composition to obtain solution or dispersion of the microbiocide in the resin. When heating and mixing the composition, the melting point and viscosity of the resin composition is reduced as compared to the resin per se. It has been found that homogeneous resin-microbiocide compositions containing high concentrations of the microbiocide can be formed in this manner. In addition, it has been found that 10,10′-oxybisphenoxarsine and 2,3,5,6-tetrachloro-4-(methylsulfonyl) pyridine function as a heat stabilizer for polyvinyl chloride-polyvinyl acetate copolymers and homopolymer.

Representative suitable thermoplastic resins that can be employed to form the microbiocide-resin composition or which can be compounded with the microbiocide-resin composition include polyvinyl chloride, vinyl chloride-vinyl acetate copolymers, polyurethanes, polyamides, polyolefins, polystyrene, vinyl chloride-acrylonitrile copolymers, polyesters and the like.

Suitable microbiocides include:

OBPA — 10,10′-oxybisphenoxarsine
Vancide 89 — N-(trichloromethylthio)-4-cyclohexene-1,2-dicarboximide
Dowcil S-13 — 2,3,5,6-tetrachloro-4-(methylsulfonyl) pyridine
Dowcil A-40 — 2,3,5-trichloro-4-propylsulfonyl pyridine
Zinc Omadine — zinc salt of 1-hydroxypyridine-2-thione
Fungitrol 11 — N-(trichloromethylthio) phthalimide
Difolatan — cis-N-(1,1,2,2-tetrachloroethyl)-thio-4-cyclohexene-1,2-dicarboximide
Isolan — 1-isoprppyl-3-methyl pyrazolyl-5-dimethyl carbamate
3-methyl-pyrazolyl dimethylcarbamate
Maneb — manganese ethylene bixdithiocarbamate
Zineb — zinc analog of Maneb
Nabam — disodium analog of Maneb
Ferbam — ferric dimethyl dithiocarbamate
Ziram — zinc alanog of Ferbam
Karathane — 2,4-dinitro-6-capryl phenol crotonate
Ovotran — p-chlorophenyl-p-chlorobenzenesulphonate
Skane M-8 — 2-N-octyl-4-isothiazolin-3-one
Benomyl — methyl-1(butylcarbamoyl)-2 benzimidazole carbamate
Metasol TK-100 — 2-(4-thiazolyl) benzimidazole
Copper-8 — copper 8-hydroxy-quinolinate
α-diethoxyphosphinodithioacetylurea
α-dimethoxyphosphinodithioacetylurea
Diethoxyphosphinodithioacetamide
Dimethoxyphosphinodithioacetamide
Bis(dimethylamido) phosphoryl fluoride
Tributyl tin fluoride and mixtures thereof. The preferred microbiocides are 10,10′-oxybisphenoxarsine, N-(trichloromethylthio)-4-cyclohexene-1,2-dicarboximide, 2,3,5,6-tetrachloro-4-(methylsulfonyl) pyridine and N-(trichloromethylthio) phthalimide since they are relatively easy to incorporate into a wide variety of resins at high concentration without significant loss of microbiological activity and without significant degradation to the resin.

The microbiocide and resin are mixed under conditions of heating to melt and to soften the resin and to form a homogeneous mixture wherein upon cooling the microbiocide is rendered far less migratory by the resin matrix. The mixture is subjected to shear forces and heat in any suitable apparatus such as a two-roll mill or a Banbury mixer or extruder and the resultant softened composition is formed such as by extrusion, milling or calendering. The formed composition is cooled so that it can be broken up into small particles thereby permitting its subsequent incorporation into other thermoplastic compositions having an effective low concentration of the microbiocides.

The compositions of this invention are blended with a second thermoplastic composition by conventional means. The concentrated microbiocide-resin composition can be added during compounding of the second thermoplastic composition or can be incorporated therein after it has been compounded but prior to fabrication of the second thermoplastic composition in any conventional manner such as extrusion, melting or calendering. All that is required is that the microbiocide-containing composition and the second thermpolastic composition be compatible so that a homogeneous final composition results. The microbiocide-containing composition should have a softening temperature below or within the range of temperatures encountered during conventional processing of the second thermoplastic composition. These temperatures are within the range of between about 250° F and about 500° F. It is preferred that the resin-microbiocide concentrates have a softening temperature within a range of about 150° F to 300° F.

In forming the microbiocide-containing composition of this invention, the usual resin additives optionally can be included. If desired, a plasticizer for the resin can be incorporated with the composition. However, it has been found that when higher concentrations of microbiocide are employed, reduced concentration of plasticizer must be employed to avoid incompatibility of the microbiocide and resin. The concentration of plasticizer that can be tolerated in the compositions of this invention also is dependent upon the chemical compositions of the resin, the plasticizer and the microbiocide. Generally, moderate plasticizer concentrations can be tolerated within the range of between about 5 and 20 weight % when the microbiocides are employed at concentrations of 50 weight % or above. Higher plasticizer concentrations can be employed with lower concentrations of microbiocide. Thus, while the compositions of this invention can be made without plasticizers, it should be noted that is is not intended that this invention is limited by their exclusion. To determine suitable plasticizers of a particular resin-microbiocide system, all that is necessary is that one add the plasticizer, within the range noted above, to the resin-microbiocide composition, mix the resultant composition and visually determine whether the microbiocide has been immobilized by the resin to form a homogeneous composition. Any of the conventional resin plasticizers can be employed including diakyl phthalates, epoxy plasticizers, polyester plasticizers, diakyl phosphites and the like. In addition, the usual resin additives can be included such as ultraviolet stabilizer, heat stabilizer, fillers, dyes, pigments, lubricants and the like.

In a preferred aspect of this invention, the concentrated microbiocide-resin composition is formed with a vinyl chloride-vinyl acetate copolymer and the microbiocide, preferably 10,10'-oxybisphenoxarsine (OBPA), and is incorporated into a second thermoplastic resin having a composition different than the chloride-vinyl acetate copolymer employed to form the concentrate. It has been found that the final composition produced thereby contains the microbiocide homogeneously distributed therein in effective concentrations while minimizing or eliminating the need for a plasticizer during compounding of the final composition. This is desirable since some thermoplastic resins such as polyurethanes can tolerate only very small concentrations of a plasticizer, if any, to avoid physical degradation of the thermoplastic resins. In addition, as noted above, the presence of a plasticizer may cause undesirable blooming of the microbiocide in the resin and so that minimizing or eliminating the use of a plasticizer is desirable in forming a final product having desirable physical characteristics and which is protected against microbiological attack. Particularly desirable products are obtained when the second thermoplastic resin is polyurethane, polyvinyl chloride or polyethylene. Although any of the microbiocides set forth above are useful in forming these final products, OBPA is preferred since it has high microbiocidal activity and so that only small concentrations of the concentrate are required to obtain homogeneous dispersion of OBPA at effective concentrations. In this embodiment, the PVC/PVA based concentrate is employed in amounts of between about 0.5 and 5.0 weight percent based upon the total composition. In a specific embodiment, the concentrate is formed from about 95 parts vinyl chloride-vinyl acetate copolymer and about 5 parts OBPA which optionally can contain about 0.1 parts of a lubricant such as stearic acid or zinc stearate. About 1 part of this concentrate then is compounded into about 99 parts of a second thermoplastic resin composition such as polyvinyl chloride, polyurethane or polyethylene which optionally can contain the usual resin additives set forth above.

The following examples illustrate the present invention and are not intended to limit the same.

EXAMPLE I

This example illustrates that Dowcil S-13 can be incorporated into thermoplastic resins either in the absence or in the presence of a plasticizer.

Each of the formulations set forth below in Table I were blended in a Henschel mixer at temperature ranging from about 70° F to 220° F for a period of 1 to 10 minutes to form a homogeneous powder blend. In each instance, the thermoplastic resin, in particulate form, was added to the Henschel mixer together with the other plastic additive, if any, and microbiocide. After the thermoplastic resin composition had been mixed, it was extruded at a temperature between 150° F and 300° F into a rod form which then was cooled to room temperature. The rod then was pelletized. Compatability was determined by sheeting a portion of the pellets and visually observing whether blooming had occurred over a period of up to two months at one week intervals. Extrusion properties were determined by the ability of the composition to retain its rod form for subsequent pelletization.

Table I

| Sample No. | 1 | 2 | 3 | 4 | 5 | 6 | 7 |
|---|---|---|---|---|---|---|---|
| (Parts by weight) | | | | | | | |
| PVC (low MW) | 100.0 | 100.0 | 100.0 | | 47 | | |
| Copolymer VYHH PVC/VA (86:14) | | | | 46.75 | | 100 | 100 |
| Ba, Cd, Zn Stabilizer-(Mark KCB) | 3.0 | 3.0 | 1.0 | | | | |
| Stearic Acid | 0.5 | 0.5 | 1.0 | 0.25 | | | |
| Dioctyl Phthalate | 15.0 | | | | | 15 | |
| Dipropylene Glycol Dibenzoate | | 15.0 | | | | | |
| Dowcil S-13 | 17.8 | 17.8 | 306.0 | 53.0 | 53.0 | 25 | 20 |
| Compatibility | I | C | C | C | C | C | C |
| Extrusion properties | NG | G | G | NG | G | G | G |
| Milling properties | G | G | G | G | G | G | G |

I = Incompatible or Surface Blooming
C = Compatible
NG = Not Good
G = Good

As shown in Table I, Dowcil S-13 is compatible in vinyl chloride-vinyl acetate copolymers or vinyl chloride hompolymers at high levels without a plasticizer. However, surface blooming results when 15 parts of dioctyl phthalate plasticizer and 0.5 parts of stearic acid lubricant are included in the composition while compatibility and no blooming result when employing 15 parts of the same plasticizer without the stearic acid lubricant. In each instance, the resin-microbiocide composition can be formed by extrusion and/or milling.

Samples 1 through 7 are compatible with thermoplastic polymers to form compositions containing an effective concentration of Dowcil S-13 including vinyl chloride homopolymers, polyethylene polyvinyl acetate, polyurethane, vinyl chloride-vinyl acetate copolymers and thermoplastic rubbers such as chlorinated polyethylene and nitrile rubbers.

To determine microbiological activity of the Dowcil S-13- resin concentrate of this invention, 1.5 weight percent of sample 5, based on total weight was blended with the resin composition employed for such testing in Example III by the blending process described in Example III. The testing procedures and the bacteria and fungi tested were those set forth in Example III including a 500 hour weather test. The results are set forth in Table Ia.

TABLE Ia

Antimicrobiocidal Activity
Zone of Inhibition (mm)/Stain or Growth

| Sample 5 + PVC | Staph. Aureus | K. pneumonial | Pink Stain | Mixed Spore |
|---|---|---|---|---|
| Unleached | 7/NGCA | 1/NGCA | 8/NS | 3/NG |
| Leached | 7/NGCA | 1/NGCA | 8/NS | 3/NG |
| Weathered 100 Hours | 5/NGCA | 0.5/NGCA | 5/NS | 2/NG |
| Weathered 200 Hours | 6/NGCA | 0.5/NGCA | 5/NS | 0/NG |
| Weathered 300 Hours | 0/LS | 0/LG | 0/HS | 0/LG |
| Weathered 500 Hours | 0/HS | | | 0/LG |

NGCA = No Growth Contact Area
NS = No Stain
NG = No Growth
LG = Low Growth
HS = Heavy Stain
LS = Light Stain As shown in Table Ia, the film showed good antifungal activity both before and after weathering and no evidence of stain up to 200 hours of weathering.

EXAMPLE II

This example illustrates that Vancide-89 can be incorporated into thermoplastic resins either in the absence or in the presence of a plasticizer.

Each of the formulations set forth below in Table II were blended in a Henschel mixer, except Sample 9, which was blended in a two roll mill at about 250° F. Temperatures in the Henschel mixer ranged from 70° F to 220° F. Mixing times ranged from 1 to 10 minutes. In each instance, the thermoplastic polymer in particulate form was added to the Henschel mixer or the two roll mill, together with the microbiocide and other plastic additives set forth, if any. After the composition had been mixed, it was extruded at a temperature between 150° F and 300° F and extruded into a 2.5 mil thick sheet. Compatibility was determined by visually observing whether blooming had occured over a period of up to two months at one week intervals. Extrusion properties were determined by the ability of the composition to retain its sheet form for subsequent pelletization.

Table II

| Sample No. | 8 | 9 | 10 | 11 | 12 |
|---|---|---|---|---|---|
| (Parts by Weight) | | | | | |
| PVC (Low MW) | 100.0 | 100.0 | 100.0 | | |
| Compolymer VYHH PCV/VA 86:14 | | | | 49.75 | 100 |
| Ba, Cd, Zn, Stabilizer - (Mark KCB) | 3.0 | 3.0 | 3.0 | | |
| Stearic Acid | 0.5 | 0.5 | 0.5 | 0.25 | |
| Dioctyl Phthalate | 15.0 | | 15.0 | | 15 |
| Vancide-89 | 17.8 | 17.8 | 118.5 | 50.0 | 25 |
| Mark 275 Tin Stabilizer | | | | | 0.5 |
| Compatibility | I | C | C | C | C |
| Extrusion Properties | NG | NG | NG | G | G |
| Milling Properties | G | G | G | G | G |

I = Incompatible
C = Compatible
NG = Not Good
G = Good

As shown in Table II, Vancide-89 is compatible in vinyl chloride-vinyl acetate copolymer or polyvinyl chloride at high levels with or without a plasticizer. Incompatibility results when 15 parts of dioctyl phthalate plasticizer is included in the composition.

In each instance, the resin-microbiocide composition can be formed by extrusion and/or milling. Samples 8 through 12 are compatible with thermoplastic polymers to form compositions containing an effective concentration of Vancide-89 including polyvinyl chloride, polyethylene, polyvinyl acetate, polyurethane, vinyl chloride-vinyl acetate copolymers and thermoplastic rubbers such as chlorinated polyethylene and nitrile rubbers.

To determine microbiological activity of the Vancide-89-resin concentrate of this invention, 1 weight percent of Sample 11, based on total weight was blended with the resin composition employed for such testing in Example III by the blending process described in Example III. The testing procedures and the bacteria and fungi tested were those set forth in Example III but omitting the 300 hour weather test. The results are set forth in Table IIa.

TABLE IIa

| | Antimicrobiocidal Activity Zone of Inhibition (mm)/Stain or Growth | | | |
|---|---|---|---|---|
| Sample 11 + PVC | Staph Aureus | K. pneumonial | Pink Stain | Mixed Spore |
| Unleached | 4/NGCA | 0/NGCA | 0.5/NS | 2/NG |
| Leached | 4/NGCA | 0/NGCA | 0.5/NS | 2/NG |
| Weathered 100 Hours | 4/NGCA | 0/NGCA | 0/NS | 1/NG |

TABLE IIa-continued

| | Antimicrobiocidal Activity Zone of Inhibition (mm)/Stain or Growth | | | |
|---|---|---|---|---|
| Sample 11 + PVC | Staph Aureus | K. pneumonial | Pink Stain | Mixed Spore |
| Weathered 200 Hours | 3/NGCA | 0/NGCA | 0/TrS | 1/NG |

NGCA = No Growth Contact Area
NG = No Growth
NS = No Stain
TrS = Trace Stain

As shown in Table IIa, the film showed good antifungal and antibacterial activity both before and after weathering.

EXAMPLE III

This example illustrates that OBPA can be incorporated into thermoplastic resins either in the absence or in the presence of a plasticizer.

Each of the formulations set forth below in Table III were blended in a Henschel mixer at a temperature ranging from about 70° F to 210° F for a period of 1 to 10 minutes. In each instance, the thermoplastic polymer in particulate form was added to the Henschel mixer together with microbiocide and the other plastic additives set forth, if any. After the composition had been mixed, it was extruded into a 25 ml thick sheet. Compatibility was determined by visually observing whether blooming had occurred over a period of up to two months at one week intervals. Extension properties were determined by the ability of the composition to retain its sheet form for subsequent pelletization.

TABLE III

| Sample No. | 13 | 14 | 15 | 16 | 16a | 16b |
|---|---|---|---|---|---|---|
| PVC (Low MW) | 100.0 | 29.0 | | | 100 | |
| PVC/VA Copolymer | | | 95 | 100 | | 100 |
| Ba, Cd, Zn, Stabilizer | 3.0 | 0.50 | | | 0.5 | 0.5 |
| Stearic Acid | 0.25 | 0.5 | | | | |
| Dioctyl Phthalate | 50.0 | | | | 25 | 25 |
| OBPA | 11.1 | 77.7 | 5.5 | 50 | 6.6 | 6.6 |
| Compatibility | I | C | C | G | G | G |
| Extrusion Properties | G | | G | G | G | G |
| Milling Properties | G | G | G | G | G | G |

I = Incompatible
C = Compatible
G = Good

As shown in Table III, OBPA is compatible in vinyl chloride-vinyl acetate copolymers or polyvinyl chloride at high levels with or without a plasticizer. However, incompatibility results when 50 parts of dioctyl phthalate plasticizer is included in the polyvinyl chloride composition. In each instance, the resin-microbiocide composition can be formed by extrusion and/or milling.

Samples 13 through 16 are compatible with thermoplastic polymers to form compositions containing an effective concentration of OBPA including polyvinyl chloride, polyethylene, polyvinyl acetate, polyurethane, vinyl chloride-vinyl acetate copolymers and thermoplastic rubbers such as chlorinated polyethylene and nitrile rubbers.

To determine microbiological activity of the OBPA-resin concentrate of this invention, 1 weight percent of a sample 15 based on total weight was blended with a resin composition comprising 100 parts by weight PVC, 3.5 parts Mark KCV (barium-cadmium-zinc heat stabilizer), 1.5 parts Mark C (phosphite chelate), 1.0 parts Mark 202A (V.V. stabilizer), 0.25 stearic acid, 40 parts dioctyl phthalate and 7.7 parts expoxidized soybean oil to obtain a final composition containing 0.05% OBPA. Blending was effected at about 72° F (ambient temperature) and the resultant composition was calendered to form the resin film. The film was tested for microbiological activity both before and after weathering and leached or unleached against *Staph. aureus,* 209 ATCC 6538; K. pneumonial, ATCC 4352; Pink stain, *Str. recticulum* ATCC 25607 and a mixed fungal spore of *Aspergillus niger,* ATCC 9642, *Aspergillus flavus,* ATCC 9643, pencillium, ATCC 9644 and *Chaetomium globosum,* ATCC 6205. The leached film was placed in a water reservoir with at least 5 changes of water for 24 hours wherein the water was 80°–85° F. The weathered samples were exposed to 100 or 200 or 300 hours of accelerated weathering in an Atlas-XW-W Xenon arc Weather-Ometer programmed (No. 7 cam per ASTM-G-26-70) for continuous light with 18 minutes of water spray every two hours.

Test specimens were placed on nutrient agar inoculated with the bacterial and fungal test organisms. After incubation (bacteria 24 hours at 37° C, fungi — 14 days at 28° C), antimicrobiocidal activity was evaluated by measuring the size of the clear zone of no growth around the sample and rating the degree of growth or stain visually. The results are shown in Table IIIa.

TABLE IIIa

Antimicrobiocidal Activity
Zone of Inhibition (mm)/Stain or Growth

| Sample 15 + PVC | Staph Aureus | K. pneumonial | Pink Stain | Mixed Spore |
|---|---|---|---|---|
| Unleached | 9/NGCA | 5/NGCA | 5/NS | 6/NG |
| Leached | 9/NGCA | 4/NGCA | 5/NS | 6/NG |
| Weathered 100 Hours | 8/NGCA | 1/NGCA | 3/NS | 2/NG |
| Weathered 200 Hours | 6/NGCA | 1/NGCA | 1/NS | 2/NG |
| Weathered 300 Hours | | | 0/TrS | 0/NG |

NCGA = No Growth Contact Area
NS = No Stain
NG = No Growth
TrS = Trace Stain

As shown in Table IIIa, the film showed good antifungal and antibacterial activity both before and after weathering.

EXAMPLE IV

This example illustrates the nontoxic nature of the compositions of this invention.

A solid composition was prepared by mixing 2,371 grams of a vinyl chloride — 16.8 wt. % vinyl acetate copolymer and 129 grams 10,10' OBPA (containing 3 wt. % DOP). The resultant homogeneous composition was extruded into a rod and pelletized. The pellets were tested for oral and dermal toxicity by the procedures described below.

Adult male rats of the Sprague-Dawley strain, weighing 150–250 grams were fasted for 24 hours, then given a single calculated dose of the above-described composition and placed in screen bottom cages with free access to water and laboratory food for a two week observation period. The solid composition was mixed with the laboratory food in a weight ratio of 1:4. The results are shown in Table IV.

TABLE IV

| Dosage level of OBPA-Copolymer (gm/kg) | Mortality | |
|---|---|---|
| | Number | Day |
| 5 | 0/6 | |
| 10 | 0/6 | |
| 20 | 0/6 | |

As shown in Table IV, no mortality was observed in the test rats even at levels as high as 20 gm per kg of body weight. Thus, the solid composition has a surprisingly high Oral $LD_{50}$ level in excess of 20 gm/kg. In contrast, OBPA has an Oral $LD_{50}$ of 15 milligram/kg.

The test for dermal toxicity was conducted with male rabbits. The animals were housed in individual screen bottom cages and supplied with water and laboratory food ad libitum and the OBPA-copolymer composition inserted under a sleeve of rubber snugly fastened about the clipped trunk of the test animal. The animals were immobilized for a 24 hour period immediately following the treatment. At the end of the exposure period, the sleeves were removed and the test animals returned to cages for a two week observation period during which evidences of toxicity were noted and mortality data tabulated as shown in Table V.

TABLE V

| Animal Number | Dose (gm/kg) | Body Weight (gms) | | |
|---|---|---|---|---|
| | | Initial | 1 Week | 2 Weeks |
| 1 | 2 | 2970 | 2950 | 3142 |
| 2 | 2 | 3650 | 3774 | 3846 |
| 3 | 4 | 2960 | 3329 | 3512 |
| 4 | 4 | 3140 | 3247 | 3510 |
| 5 | 8 | 3095 | 3230 | 3260 |
| 6 | 8 | 3355 | 3557 | 3585 |

No mortalities were observed during the test period. Thus, the dermal toxicity of the test composition is in excess of 8 gm/kg.

EXAMPLE V

This example illustrates that Fungitrol-11 and Zinc Omadine can be incorporated in high concentrations in polyvinyl chloride, homopolymer and polyvinyl chloride-polyvinyl acetate copolymer containing from about 10 to 18 weight % polyvinyl acetate and provide antimicrobicidal activity.

The compositions in Table VI were blended to form a miocrobiocide concentrate, subsequently blended with polyvinyl chloride to form a film containing the microbiocide at its normal usage concentration and the film then was tested for microbiological activity. The initial concentrates were prepared by physically mixing the resin, microbiocide and 1% Mark 275 tin stabilizer in a Hobart Blender for 5 minutes. The dry blends were formed into strands on a Rheocard extruder at 50 RPm screw speed with a ⅛ inch diameter die. The strands were allowed to cool to room temperature and then were ground into small irregular particles. The compositions dry-blended and extruded are shown in Table VI.

TABLE VI

| Microbiocide | Weight % Microbiocide | Resin | Extrusion Temperature, ° C |
|---|---|---|---|
| Fungitrol-11 | 35 | PVC/PVA | 110, 115, 120, 125 |
| Fungitrol-11 | 50 | PVC/PVA | 110, 115, 125, 130 |
| Fungitrol-11 | 35 | PVC | 120, 120, 125, 135 |
| Fungitrol-11 | 50 | PVC | 120, 120, 125, 135 |
| Zinc Omadine | 5 | PVC/PVA | 110, 120, 135, 135 |
| Zinc Omadine | 10 | PVC/PVA | 110, 120, 125, 125 |
| Zinc Omadine | 20 | PVC/PVA | 110, 120, 125, 135 |
| Zinc Omadine | 10 | PVC | 110, 120, 125, 135 |
| Zinc Omadine | 20 | PVC | 110, 120, 125, 135 |

In each instance, a homogeneous composition was formed which could be incorporated subsequently into a polyvinyl chloride composition to form a resin composition having microbiocidal activity at the normal usage concentration of the microbiocide.

The PVC resin composition with which the concentrates set forth above were blended comprises 100 parts PVC, 3.5 parts Mark KCB (borium-cadmium-zinc heat stabilizer), 1.5 parts phosphite chelate, 1.0 parts Mark 202A (UV stabilizer), 0.25 parts stearic acid, 40 parts dioctyl phthalate and 7.7 parts epoxidized soybean oil. This composition was blended with 1.5 weight % of the Fungitrol-11 composition formed from PVC and containing 50% Fungitrol-11 to form a composition containing 0.75 weight % Fungitrol-11 or was blended with 1.0 weight % of the Zinc Omadine composition formed from PVC and containing 20% Zinc Omadine to form a composition containing 0.20 weight % of Zinc Omadine. Blending was effected at about 72° F (ambient temperature) and the resultant compositions were milled to form the resin film. These films were tested for microbiological activity both before and after weathering against *Staph. aureus*, 209 ATCC 6538; *K. pneumonial*, ATCC 4252; Pink stain, *Str. reticulum* ATCC 25607 and a mixed fungal spore of *Aspergillus niger*, ATCC 9642, *Aspergillus flavus*, ATCC 9643, *Penicillium funiculosum*, ATCC 9644 and *Chaetomium globosum*, ATCC 6205. The weathered samples were exposed to 100 hours of accelerated weathering in an Atlas 600-XW-W Xenon arc Weather Ometer, programmed (No. 7 cam per ASTM-G-26-70) for continuous light with 18 minutes of water spray every 2 hours.

Test specimens were placed on nutrient agar inoculated with the bacterial and fungal test organisms. After incubation (bacteria — 24 hours at 37° C, fungi — 14 days at 28° C), antimicrobiocidal activity was evaluated by measuring the size of the clear zone of no growth around the sample and rating the degree of growth or stain visually. The results are shown in Table VII.

TABLE VII

Antimicrobiocidal Activity
Zone of Inhibitions (mm)/Stain or Growth

| Microbiocide | Staph. aureus | K. pneumonial | Pink Stain | Mixed Spore |
|---|---|---|---|---|
| Fungitrol-11 | | | | |
| Unweathered | 2/NGCA | 0/NGCA | 0/NS | 3/NG |
| Weathered - 100 hrs. | 1/NGCA | 0/NGCA | 0/NS | 3/NG |
| Zinc Omadine | | | | |
| Unweathered | 7/NGCA | 2.5/NGCA | 5/NS | 2/NG |
| Weathered - 100 hrs. | 0/GCA | 0/GCA | 0/HS | 0/MG |

NGCA = No Growth in Contact Area
GCA = Growth in Contact Area
NS = No Stain
NG = No Growth
HS = Heavy Stain
MG = Moderate Growth As shown in Table VII, the PVC film containing the Fungitrol-11 concentrate showed good antifungal activity to mixed fungi before and after weathering and no evidence of stain. At the concentration used (0.75%), antibacterial activity was shown to *Staph. aureus*, but not to the gram negative *K. pneumonial*. The PVC film containing Zinc Omadine showed excellent antimicrobial activity before weathering to all of the bacterial and fungal test organisms. Activity was lost after 100 hours of weathering.

EXAMPLE VI

This example illustrates that tributyl tin fluoride can be incorporated into thermoplastic resins in high concentrations.

Each of the formulations set forth in Table VIII were mixed in a Hobart Blender for 5 minutes at about 72° F (ambient temperature). Each resin was added to the blender in particulate form with 1 weight % Mark 275 (tin stabilizer) and the tributyl tin fluoride. The resultant compositions were extruded on a Rheocard extruder at the temperatures shown in Table VIII to form strands. The extruder was operated at 50 RPM screw speed with a ⅛ inch diameter die. The strands were visually evaluated and then ground to small irregular particles, added to a polyvinyl chloride composition, processed into films and were found to impart microbiocidal activity to the films.

TABLE VIII

| Resin | Weight % Tributyl Tin Fluoride | Extrusion Temperatures, ° C | Appearance |
|---|---|---|---|
| PVC/PVA | 10 | 120, 135, 140, 150 | Homogeneous white opaque solid suspension of tributyl tin fluoride with resin; smooth surface |
| PVC/PVA | 20 | 125, 135, 135, 140 | Homogeneous white opaque solid suspension of tributyl tin fluoride with resin; smooth surface |
| PVC | 10 | 140, 145, 155, 155 | Homogeneous white opaque solid suspension of tributyl tin fluoride with resin; rough surface |

It was found that tributyl tin fluoride was more easily homogeneously added to PVC/PVA than to PVC to form a homogeneous composition wherein the tributyl tin fluoride is dispersed into the resins. All of the composition formed were satisfactory as resin-microbiocidal concentrates.

We claim:

1. A solid composition consisting essentially of a homogeneous melt blended mixture of a solid thermoplastic resin and from 1 to 80 weight percent of a microbiocide based upon the weight of said solid composition which is present in the mixture at a concentration of at least about 20 times greater than the normal upper usage concentration of the microbiocide and wherein said microbiocide is immobilized and rendered physiologically inert in said resin, the concentration of said microbiocide in said mixture being sufficient to render a second thermoplastic composition resistant to microbiological degradation when said mixture is added to said second thermoplastic composition at a sufficiently low concentration to render said mixture and said second thermoplastic composition compatible.

2. The solid composition of claim 1 in particulate form.

3. The solid composition of claim 1 which contains a plasticizer for said solid thermoplastic resin.

4. The solid composition of claim 2 which contains a plasticizer for said solid thermoplastic resin.

5. The solid composition of claim 1 wherein the microbiocide is 10,10'-oxybisphenoxarsine.

6. The solid composition of claim 2 wherein the microbiocide is 10,10'-oxybisphenoxarsine.

7. The solid composition of claim 1 wherein the microbiocide is N-(trichloromethylthio)-4-cyclohexene-1,2-dicarboxamide.

8. The solid composition of claim 2 wherein the microbiocide is N-(trichloromethylthio)-4-cyclohexene-1,2-dicarboxamide.

9. The solid composition of claim 1 wherein the microbiocide is 2,3,5,6-tetrachloro-4-(methylsulfonyl) pyridine.

10. The solid composition of claim 2 wherein the microbiocide is 2,3,5,6-tetrachloro-4-(methylsulfonyl) pyridine.

11. The solid composition of claim 1 wherein the microbiocide is N-(trichloromethylthio) phthalimide.

12. The solid composition of claim 2 wherein the microbiocide is N-(trichloromethylthio) phthalimide.

13. The solid composition of claim 1 wherein the microbiocide is tributyl tin fluoride.

14. The solid composition of claim 2 wherein the microbiocide is tributyl tin fluoride.

15. The solid composition of claim 1 wherein the solid thermoplastic resin is polyvinyl chloride.

16. The solid composition of claim 2 wherein the solid thermoplastic resin is polyvinyl chloride.

17. The solid composition of claim 1 wherein the solid thermoplastic resin is a copolymer of vinyl chloride and vinyl acetate.

18. The solid composition of claim 2 wherein the solid thermoplastic resin is a copolymer of viny chloride and vinyl acetate.

19. The solid composition of claim 6 wherein the said thermoplastic resin is polyvinyl chloride.

20. The solid composition of claim 8 wherein the solid thermoplastic resin is polyvinyl chloride.

21. The solid composition of claim 10 wherein the solid thermoplastic resin is polyvinyl chloride.

22. The solid composition of claim 6 wherein the solid thermoplastic resin is a copolymer of vinyl chloride and vinyl acetate.

23. The solid composition of claim 8 wherein the solid thermoplastic resin is a copolymer of vinyl chloride and vinyl acetate.

24. The solid composition of claim 10 wherein the solid thermoplastic resin is a copolymer of vinyl chloride and vinyl acetate.

25. The process for forming a solid thermoplastic composition containing an effective concentration of a microbiocide but at a concentration less than that which presents a toxicological hazard which comprises mixing a particulate microbiocidally active composition consisting essentially of a homogeneous melt blended mixture of a first solid thermoplastic resin and from 1 to 80 weight percent of a microbiocide based upon the weight of said first thermoplastic resin which is present in the mixture at a concentration of at least 20 times greater than the normal upper usage concentration of the microbiocide and wherein said microbiocide is immobilized and rendered physiologically inert in said first resin, with a second thermoplastic composition at a temperature above the softening temperature of the microbiocidally active composition and the second thermoplastic composition, the concentration of the microbiocidally active composition being sufficiently low to render it compatible with said second thermoplastic composition, and cooling the mixture to form a solid containing the microbiocidally active composition and second thermoplastic resin in homogeneous admixture.

26. The process of claim 25 wherein the resin of the microbiocidally active composition is polyvinyl chloride.

27. The process of claim 25 wherein the resin of the microbiocidally active composition is a copolymer of vinyl chloride and vinyl acetate.

28. The process of claim 25 wherein the microbiocide is 10,10'-oxybisphenoxarsine.

29. The process of claim 26 wherein the microbiocide is 10,10'-oxybisphenoxarsine.

30. The process of claim 25 wherein the microbiocide is N-(trichloromethylthio)-4-cyclohexene-1,2-dicarboxamide.

31. The process of claim 26 wherein the microbiocide is N-(trichloromethylthio)-4-cyclohexene-1,2-dicarboxamide.

32. The process of claim 25 wherein the microbiocide is 2,3,5,6-tetrachloro-4-(methylsulfonyl) pyridine.

33. The process of claim 26 wherein the microbiocide is 2,3,5,6-tetrachloro-4-(methylsulfonyl) pyridine.

34. The process of claim 25 wherein the microbiocide is N-(trichloromethylthio) phthalimide.

35. The process of claim 26 wherein the microbiocide is N-(trichloromethylthio) phthalimide.

36. The process of claim 25 wherein the microbiocide is tributyl tin fluoride.

37. The process of claim 26 wherein the microbiocide is tributyl tin fluoride.

38. A thermoplastic resin composition resistant to microbiological degradation comprising between about 0.5 and 5.0 weight percent of a composition comprising vinyl chloridfe-vinyl acetate copolymer and between 1 and 80 weight percent of a first microbiocide at a concentration of at least 20 times greater than the normal upper usage concentration of the microbiocide.

wherein said first composition is homogeneously dispersed in a second thermosplastic resin composition comprising a thermoplastic resin which is not a vinyl chloride-vinyl acetate copolymer.

39. The composition of claim 38 wherein the microbiocide is 10,10'-oxybisphenoxarsine.

40. The composition of claim 38 wherein the thermoplastic resin is a polyurethane.

41. The composition of claim 38 wherein the thermoplastic resin is polyethylene.

42. The composition of claim 38 wherein the thermoplastic resin is polyvinyl chloride.

* * * * *

REEXAMINATION CERTIFICATE (877th)

United States Patent [19]

Rei et al.

[11] B1 4,086,297

[45] Certificate Issued   Jun. 28, 1988

[54] METHOD OF MAKING POLYMERIC COMPOSITIONS AND COMPOSITIONS THEREFOR

[75] Inventors: Nuno M. Rei, Peabody; Nicholas J. Hill, Andover, both of Mass.

[73] Assignee: Ventron Corporation, Beverly, Mass.

Reexamination Request:
No. 90/001,278, Jul. 10, 1987

Reexamination Certificate for:
| | |
|---|---|
| Patent No.: | 4,086,297 |
| Issued: | Apr. 25, 1978 |
| Appl. No.: | 736,968 |
| Filed: | Oct. 29, 1976 |

Related U.S. Application Data

[63] Continuation-in-part of Ser. No. 635,755, Nov. 28, 1975, abandoned.

[51] Int. Cl.$^4$ .................. C08K 5/43; C08K 5/39; C08K 5/34; C08K 5/53
[52] U.S. Cl. .................. 524/330; 523/122; 524/94; 524/99; 524/177; 524/178; 524/507; 524/524
[58] Field of Search .................. 523/122

[56] References Cited

U.S. PATENT DOCUMENTS

| | | | |
|---|---|---|---|
| 2,490,100 | 12/1949 | Smith | 106/15 |
| 2,621,143 | 12/1952 | Goodhue et al. | 424/30 |
| 2,704,246 | 3/1955 | Goodhue et al. | 71/2.7 |
| 2,792,394 | 1/1954 | Himel et al. | 260/247.1 |
| 2,862,850 | 12/1958 | Goodhue | 424/30 |
| 2,919,200 | 3/1955 | Dubin et al. | 106/15 |
| 2,921,917 | 1/1960 | Longman | 260/23 |
| 2,941,879 | 6/1960 | Goodhue | 71/2.7 |
| 2,951,766 | 9/1960 | White | 106/15 |
| 3,005,720 | 10/1961 | Teller | 106/15 |
| 3,020,259 | 2/1962 | Schulde et al. | 260/45.95 |
| 3,105,060 | 9/1963 | Schramm et al. | 260/45.75 |
| 3,252,858 | 5/1966 | Goodhue | 424/30 |
| 3,257,351 | 6/1966 | Kraus et al. | 260/41 |
| 3,269,902 | 8/1966 | Goodhue et al. | 424/30 |
| 3,288,674 | 11/1966 | Yeager | 167/42 |
| 3,318,876 | 5/1967 | Folkemer et al. | 167/42 |
| 3,360,431 | 12/1967 | Yeager | 167/30 |
| 3,367,898 | 3/1965 | Cadmus | 260/29.6 |
| 3,401,185 | 9/1968 | Meinhardt | 260/429.9 |
| 3,422,155 | 1/1969 | Dowhenko | 260/648 |
| 3,426,133 | 2/1969 | Shotton | 424/30 |
| 3,509,212 | 4/1970 | Fonken et al. | 260/561 |
| 3,534,064 | 10/1910 | Dietrich et al. | 260/338 |
| 3,541,162 | 11/1970 | Larkin et al. | 260/633 |
| 3,549,702 | 12/1970 | Loeu | 260/566 |
| 3,635,994 | 1/1972 | Domenico | 260/294.8 |
| 3,689,449 | 4/1971 | Yeager et al. | 260/33.4 P |
| 3,694,543 | 9/1972 | Needham et al. | 424/30 |
| 3,911,135 | 10/1975 | Tirpak et al. | 424/274 |
| 3,987,700 | 10/1974 | Kalogris | 260/45.95 H |
| 4,025,690 | 5/1977 | Nanni | 428/407 |
| 4,116,908 | 9/1978 | Emery | 260/23 X A |

FOREIGN PATENT DOCUMENTS

| | | |
|---|---|---|
| 2501808 | 7/1975 | Fed. Rep. of Germany . |
| 1197851 | 6/1959 | France . |
| 4741 | of 1957 | Japan . |
| 15599 | of 1966 | Japan . |
| 14811 | of 1968 | Japan . |
| 7623 | of 1972 | Japan . |
| 50-109937 | 8/1975 | Japan . |
| 7109307 | 1/1972 | Netherlands . |
| 1219955 | of 1957 | United Kingdom . |
| 1113513 | 5/1958 | United Kingdom . |
| 00871228 | 6/1961 | United Kingdom . |
| 1085970 | 10/1967 | United Kingdom . |
| 1220165 | 1/1971 | United Kingdom . |
| 1274145 | of 1972 | United Kingdom . |
| 1333486 | 10/1973 | United Kingdom . |
| 1347346 | 2/1974 | United Kingdom . |
| 1348340 | 3/1974 | United Kingdom . |
| 1399204 | 6/1975 | United Kingdom . |
| 1480125 | 7/1977 | United Kingdom . |
| 1502411 | of 1978 | United Kingdom . |

OTHER PUBLICATIONS

Ralph Elsonschiml & William Bauer "Microbial Degradation of Plasticized Vinyl Films", pp. 250–271.
Chem. Abs. 46825r, vol. 77 (1972).
Chem. Abs. 78707a, vol. 70 (1969).
Chem. Abs. 112965t, vol. 82 (1975).

*Primary Examiner*—V. P. Hoke

[57] ABSTRACT

A solid composition comprising a homogeneous mixture of a solid thermoplastic resin and from 1 to 80 weight % of at least one microbiocide which is insoluble in water, is readily dispersible or soluble in the resin at temperatures sufficiently high to permit plastic manipulation of the resin and the dispersion or solution of the microbiocide is sustained indefinitely upon cooling to ambient temperature while the diffusivity of the microbiocide in the resin under such conditions becomes vanishingly small, retains its microbiocidal activity in the resin and does not degrade or react with the resin in which it is dispersed. This composition provides a convenient non-toxic dosage form of the microbiocide which is subsequently mixed with a second thermoplastic resin at a concentration of about 0.5 to 15 weight % to obtain a homogeneous resin composition containing an effective amount of the microbiocide.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1 and 25 is confirmed.

Claims 2–24, 26–28, 30, 32, 34, 36 and 38–42 are determined to be patentable as amended.

Claims 29, 31, 33, 35 and 37, dependent on an amended claim, are determined to be patentable.

New claims 43–52 are added and determined to be patentable.

2. [The solid composition of claim 1] *A solid composition consisting essentially of a homogeneous melt blended mixture* in particulate form *of a solid thermoplastic resin and from 1 to 80 weight percent of a microbiocide based upon the weight of said composition which is present in the mixture at a concentration of at least about 20 times greater than the normal upper usage concentration of the microbiocide and wherein said microbiocide is immobilized and rendered physiologically inert in said resin, the concentration of said microbiocide in said mixture being sufficient to render a second thermoplastic composition resistant to microbiological degradation when said mixture is added to said second thermoplastic composition at a sufficiently low concentration to render said mixture and said second thermoplastic composition compatible.*

3. [The solid composition of claim 1 which contains] *A solid composition consisting essentially of a homogeneous melt blended mixture of a solid thermoplastic resin and from 1 to 80 weight percent of a microbiocide based upon the weight of said solid composition which is present in the mixture at a concentration of at least about 20 times greater than the normal upper usage concentration of the microbiocide and wherein said microbiocide is immobilized and rendered physiologically inert in said resin, the concentration of said microbiocide in said mixture being sufficient to render a second thermoplastic composition resistant to microbiological degradation when said mixture is added to said second thermoplastic composition at a sufficiently low concentration to render said mixture and said second thermoplastic composition compatible, said solid composition containing* a plasticizer for said solid thermoplastic resin.

4. [The solid composition of claim 2 which contains] *A solid composition consisting essentially of a homogeneous melt blended mixture in particulate form of a solid thermoplastic resin and from 1 to 80 weight percent of a microbiocide based upon the weight of said solid composition which is present in the mixture at a concentration of at least about 20 times greater than the normal upper usage concentration of the microbiocide and wherein said microbiocide is immobilized and rendered physiologically inert in said resin, the concentration of said microbiocide in said mixture being sufficient to render a second thermoplastic composition resistant to microbiological degradation when said mixture is added to said second thermoplastic composition at a sufficiently low concentration to render said mixture and said second thermoplastic composition compatible, said solid composition containing* a plasticizer for said solid thermoplastic resin.

5. [The solid composition of claim 1 wherein the microbiocide is] *A solid composition consisting essentially of a homogeneous melt blended mixture of a solid thermoplastic resin and from 1 to 80 weight percent of* 10,10'-oxybisphenoxarsine *based upon the weight of said solid composition which is present in the mixture at a concentration of at least about 20 times greater than the normal upper usage concentration of 10,10'-oxybisphenoxarsine and wherein 10,10'-oxybisphenoxarsine is immobilized and rendered physiologically inert in said resin, the concentration of 10,10'-oxybisphenoxarsine in said mixture being sufficient to render a second thermoplastic composition resistant to microbiological degradation when said mixture is added to said second thermoplastic composition at a sufficiently low concentration to render said mixture and said second thermoplastic composition compatible.*

6. [The solid composition of claim 2 wherein the microbiocide is] *A solid composition consisting essentially of a homogeneous melt blended mixture in particulate form of a solid thermoplastic resin and from 1 to 80 weight percent of* 10,10'-oxybisphenoxarsine *based upon the weight of said solid composition which is present in the mixture at a concentration of at least about 20 times greater than the normal upper usage concentration of 10,10'-oxybisphenoxarsine and wherein 10,10'-oxybisphenoxarsine is immobilized and rendered physiologically inert in said resin, the concentration of 10,10'-oxybisphenoxarsine in said mixture being sufficient to render a second thermoplastic composition resistant to microbiological degradation when said mixture is added to said second thermoplastic composition at a sufficiently low concentration to render said mixture and said second thermoplastic composition compatible.*

7. [The solid composition of claim 1 wherein the microbiocide is] *A solid composition consisting essentially of a homogeneous melt blended mixture of a solid thermoplastic resin and from 1 to 80 weight percent of* N-(trichloromethylthio)-4-cyclohexene-1,2-dicarboxamide *based upon the weight of said solid composition which is present in the mixture at a concentration of at least about 20 times greater than the normal upper usage concentration of N-(trichloromethylthio)-4-cyclohexene-1,2-dicarboxamide and wherein N-(trichloromethylthio)-4-cyclohexene-1,2-dicarboxamide is immobilized and rendered physiologically inert in said resin, the concentration of N-(trichloromethylthio)-4-cyclohexane-1,2-dicarboxamide in said mixture being sufficient to render a second thermoplastic composition resistant to microbiological degradation when said mixture is added to said second thermoplastic composition at a sufficiently low concentration to render said mixture and said second thermoplastic composition compatible.*

8. [The solid composition of claim 2 wherein the microbiocide is] *A solid composition consisting essentially of a homogeneous melt blended mixture in particulate form of a solid thermoplastic resin and from 1 to 80 weight percent of* N-(trichloromethylthio)-4-cyclohexene-1,2-dicarboxamide *based upon the weight of said solid composition which is present in the mixture at a concentration of at least about 20 times greater than the normal* upper usage concentration of N-(trichloromethylthio-4-cyclohexene-1,2-dicarboxamide and wherein N-(trichloromethylthio)-4-cyclohexene-1,2-dicarboxamide is immobilized and rendered physiologically inert in said resin, the concentration of N-(trichloromethylthio)-4-cyclohexene-1,2-dicarboxamide in said mixture being sufficient to render a second thermoplastic composition resistant to microbiological degradation when said mixture is added to said second thermoplastic composition at a sufficiently low concentration to render said mixture and said second thermoplastic composition compatible.

9. [The solid composition of claim 1 wherein the microbiocide is] *A solid composition consisting essentially of a homogeneous melt blended mixture of a solid thermoplastic resin and from 1 to 80 weight percent of* 2,3,5,6-tetrachloro-4-(methylsufonyl) pyridine *based upon the weight of said solid composition which is present in the mixture at a concentration of at least about 20 times greater than the normal upper usage concentration of* 2,3,5,6-tetrachloro-4-(methylsufonyl) pyridine *and wherein* 2,3,5,6-tetrachloro-4-(methylsufonyl) pyridine *is immobilized and rendered phsiologically inert in said resin, the concentration of* 2,3,5,6-tetrachloro-4-(methylsufonyl) pyridine *in said mixture being sufficient to render a second thermoplastic composition resistant to microbiological degradation when said mixture is added to said second thermoplastic composition at a sufficiently low concentration to render said mixture and said second thermoplastic composition compatible.*

10. [The solid composition of claim 2 wherein the microbiocide is] *A solid composition consisting essentially of a homogeneous melt blended mixture in particulate form of a solid thermoplastic resin and from 1 to 80 weight percent of* 2,3,5,6-tetrachloro-4-(methylsufonyl) pyridine *based upon the weight of said solid composition which is present in the mixture at a concentration of at least about 20 times greater than the normal upper usage concentration of* 2,3,5,6-tetrachloro-4-(methylsufonyl) pyridine *and wherein* 2,3,5,6-tetrachloro-4-(methylsufonyl) pyridine *is immobilized and rendered physiologically inert in said resin, the concentration of* 2,3,5,6-tetrachloro-4-(methylsufonyl) pyridine *in said mixture being sufficient to render a second thermoplastic composition resistant to microbiological degradation when said mixture is added to said second thermoplastic composition at a sufficiently low concentration to render said mixture and said second thermoplastic composition compatible.*

11. [The solid composition of claim 1 wherein the microbiocide is] *A solid composition consisting essentially of a homogeneous melt blended mixture of a solid thermoplastic resin and from 1 to 80 weight percent of* N-(trichloromethylthio) phthalimide *based upon the weight of said solid composition which is present in the mixture at a concentration of at least about 20 times greater than the normal upper usage concentration of N-(trichloromethylthio) phthalimide and wherein N-(trichloromethylthio) phthalimide is immobilized and rendered physiologically inert in said resin, the concentration of N-(trichloromethylthio) phthalimide in said mixture being sufficient to render a second thermoplastic composition resistant to microbiological degradation when said mixture is added to said second thermoplastic composition at a sufficiently low concentration to render said mixture and said second thermoplastic composition compatible.*

12. [The solid composition of claim 2 wherein the microbiocide is] *A solid composition consisting essentially of a homogeneous melt blended mixture in particulate form of a solid thermoplastic resin and from 1 to 80 weight percent of* N-(trichloromethylthio) phthalimide *based upon the weight of said solid composition which is present in the mixture at a concentration of at least about 20 times greater than the normal upper usage concentration of N-(trichloromethylthio) phthalimide and wherein N-(trichloromethylthio) phthalimide is immobilized and rendered physiologically inert in said resin, the concentration of N-(trichloromethylthio) phthalimide in said mixture being sufficient to render a second thermoplastic composition resistant to microbiological degradation when said mixture is added to said second thermoplastic composition at a sufficiently low concentration to render said mixture and said second thermoplastic composition compatible.*

13. [The solid composition of claim 1 wherein the microbiocide is] *A solid composition consisting essentially of a homogeneous melt blended mixture of a solid thermoplastic resin and from 1 to 80 weight percent of* tributyl tin fluoride *based upon the weight of said solid composition which is present in the mixture at a concentration of at least about 20 times greater than the normal upper usage concentration of tributyl tin fluoride and wherein tributyl tin fluoride is immobilized and rendered physiologically inert in said resin, the concentration of tributyl tin fluoride in said mixture being sufficient to render a second thermoplastic composition resistant to microbiological degradation when said mixture is added to said second thermoplastic composition at a sufficiently low concentration to render said mixture and said second thermoplastic composition compatible.*

14. [The solid composition of claim 2 wherein the microbiocide is] *A solid composition consisting essentially of a homogeneous melt blended mixture in particulate form of a solid thermoplastic resin and from 1 to 80 weight percent of* tributyl tin fluoride *based upon the weight of said solid composition which is present in the mixture at a concentration of at least about 20 times greater than the normal upper usage concentration of tributyl tin fluoride and wherein tributyl tin fluoride is immobilized and rendered physiologically inert in said resin, the concentration of tributyl tin fluoride in said mixture being sufficient to render a second thermoplastic composition resistant to microbiological degradation when said mixture is added to said second thermoplastic composition at a sufficiently low concentration to render said mixture and said second thermoplastic composition compatible.*

15. [The solid composition of claim 1 wherein the solid thermoplastic resin is] *A solid composition consisting essentially of a homogeneous melt blended mixture of a solid thermoplastic* polyvinyl chloride *resin and from 1 to 80 weight percent of a microbiocide based upon the weight of said solid composition which is present in the mixture at a concentration of at least about 20 times greater than the normal upper usage concentration of the microbiocide and wherein said microbiocide is immobilized and rendered physiologically inert in said polyvinyl chloride resin, the concentration of said microbiocide in said mixture being sufficient to render a second thermoplastic composition resistant to microbiological degradation when said mixture is added to said second thermoplastic composition at a sufficiently low concentration to render said mixture and said second thermoplastic composition compatible.*

16. [The solid composition of claim 2 wherein the solid thermoplastic resin is] *A solid composition consisting essentially of a homogeneous melt blended mixture in particulate form of a solid thermoplastic* polyvinyl chloride *resin and from 1 to 80 weight percent of a microbio-* cide based upon the weight of said solid composition which is present in the mixture at a concentration of at least about 20 times greater than the normal upper usage concentration of the microbiocide and wherein said microbiocide is immobilized and rendered physiologically inert in said polyvinyl chloride resin, the concentration of said microbiocide in said mixture being sufficient to render a second thermoplastic composition resistant to microbiological degradation when said mixture is added to said second thermoplastic composition at a sufficiently low concentration to render said mixture and said second thermoplastic composition compatible.

17. [The solid composition of claim 1 wherein the solid thermoplastic resin] *A solid composition consisting essentially of a homogeneous melt blended mixture of a solid thermoplastic resin which* is a copolymer of vinyl chloride and vinyl acetate *and from 1 to 80 weight percent of a microbiocide based upon the weight of said solid composition which is present in the mixture at a concentration of at least about 20 times greater than the normal upper usage concentration of the microbiocide and wherein said microbiocide is immobilized and rendered physiologically inert in said resin, the concentration of said microbiocide in said mixture being sufficient to render a second thermoplastic composition resistant to microbiological degradation when said mixture is added to said second thermoplastic composition at a sufficiently low concentration to render said mixture and said second thermoplastic composition compatible.*

18. [The solid composition of claim 2 wherein the solid thermoplastic resin] *A solid composition consisting essentially of a homogeneous melt blended mixture in particulate form of a solid thermoplastic resin which* is a copolymer of vinyl chloride and vinyl acetate *and from 1 to 80 weight percent of a microbiocide based upon the weight of said solid composition which is present in the mixture at a concentration of at least about 20 times greater than the normal upper usage concentration of the microbiocide and wherein said microbiocide is immobilized and rendered physiologically inert in said resin, the concentration of said microbiocide in said mixture being sufficient to render a second thermoplastic composition resistant to microbiological degradation when said mixture is added to said second thermoplastic composition at a sufficiently low concentration to render said mixture and said second thermoplastic composition compatible.*

19. [The solid composition of claim 6 wherein the said thermoplastic resin is] *A solid composition consisting essentially of a homogeneous melt blended mixture in particulate form of a solid thermoplastic polyvinyl chloride resin and from 1 to 80 weight percent of 10,10'-oxybisphenoxarsine based upon the weight of said solid composition which is present in the mixture at a concentration of at least about 20 times greater than the normal upper usage concentration of 10,10'-oxybisphenoxarsine and wherein 10,10'-oxybisphenoxarsine is immobilized and rendered physiologically inert in said polyvinyl chloride resin, the concentration of 10,10'-oxybisphenoxarsine in said mixture being sufficient to render a second thermoplastic composition resistant to microbiological degradation when said mixture is added to said second thermoplastic composition at a sufficiently low concentration to render said mixture and said second thermoplastic composition compatible.*

20. [The solid composition of claim 8 wherein the solid thermoplastic resin is] *A solid composition consisting essentially of a homogeneous melt blended mixture in particulate form of a solid thermoplastic polyvinyl chloride resin and from 1 to 80 weight percent of N-(trichloromethylthio)-4-cyclohexene-1,2-dicarboxamide based upon the weight of said solid composition which is present in the mixture at a concentration of at least about 20 times greater than the normal upper usage concentration of N-(trichloromethylthio)-4-cyclohexene-1,2-dicarboxamide and wherein N-(trichloromethylthio)-4-cyclohexene-1,2-dicarboxamide is immobilized and rendered physiologically inert in said polyvinyl chloride resin, the concentration of N-(trichloromethylthio)-4-cyclohexene-1,2-dicarboxamide in said mixture being sufficient to render a second thermoplastic composition resistant to microbiological degradation when said mixture is added to said second thermoplastic composition at a sufficiently low concentration to render said mixture and said second thermoplastic composition compatible.*

21. [The solid composition of claim 10 wherein the solid thermoplastic resin is *A solid composition consisting essentially of a homogeneous melt blended mixture in particulate form of a solid thermoplastic polyvinyl chloride resin and from 1 to 80 weight percent of 2,3,5,6-tetrachloro-4-(methylsufonyl)pyridine based upon the weight of said solid composition which is present in the mixture at a concentration of at least about 20 times greater than the normal upper usage concentration of 2,3,5,6-tetrachloro-4-(methylsufonyl)pyridine and wherein 2,3,5,6-tetrachloro-4-(methylsufonyl)pyridine is immobilized and rendered physiologically inert in said polyvinyl chloride resin, the concentration of 2,3,5,6-tetrachloro-4-(methylsufonyl)pyridine in said mixture being sufficient to render a second thermoplastic composition resistant to microbiological degradation when said mixture is added to said second thermoplastic composition at a sufficiently low concentration to render said mixture and said second thermoplastic composition compatible.*

22. [The solid composition of claim 6 wherein the solid thermoplastic resin] *A solid composition consisting essentially of a homogeneous melt blended mixture in particulate form of a solid thermoplastic resin which* is a copolymer of vinyl chloride and vinyl acetate *and from 1 to 80 weight percent of 10,10'-oxybisphenoxarsine based upon the weight of said solid composition which is present in the mixture at a concentration of at least about 20 times greater than the normal upper usage concentration of 10,10'-oxybisphenoxarsine and wherein 10,10'-oxybisphenoxarsine is immobilized and rendered physiologically inert in said resin, the concentration of 10,10'-oxybisphenoxarsine in said mixture being sufficient to render a second thermoplastic composition resistant to microbiological degradation when said mixture is added to said second thermoplastic composition at a sufficiently low concentration to render said mixture and said second thermoplastic composition compatible.*

23. [The solid composition of claim 8 wherein the solid thermoplastic resin] *A solid composition consisting essentially of a homogeneous melt blended mixture in particulate form of a solid thermoplastic resin which* is a copolymer of vinyl chloride and vinyl acetate *and from 1 to 80 weight percent of N-(trichloromethylthio)-4-cyclohexene-1,2-dicarboxamide based upon the weight of said solid composition which is present in the mixture at a concentration of at least about 20 times greater than the normal upper usage concentration of N-(trichloromethylthio)-4-cyclohexene-1,2-dicarboxamide and wherein N-(trichloromethylthio)-4-cyclohexene-1,2-dicarboxamide is immobilized and rendered physiologically inert in said resin, the concentration of N-(trichloromethylthio)-4-cyclohexene-1,2-dicarboxamide in said mixture being suf-* ficient to render a second thermoplastic composition resistant to microbiological degradation when said mixture is added to said second thermoplastic composition at a sufficiently low concentration to render said mixture and said second thermoplastic composition compatible.

24. [The solid composition of claim 10 wherein the solid thermoplastic resin] *A solid composition consisting essentially of a homogeneous melt blended mixture in particulate form of a solid thermoplastic resin which* is a copolymer of vinyl chloride and vinyl acetate *and from 1 to 80 weight percent of 2,3,5,6-tetrachloro-4-(methylsufonyl) pyridine based upon the weight of said solid composition which is present in the mixture at a concentration of at least about 20 times greater than the normal upper usage concentration of 2,3,5,6-tetrachloro-4-(methylsufonyl) pyridine and wherein 2,3,5,6-tetrachloro-4-(methylsufonyl) pyridine is immobilized and rendered physiologically inert in said resin,* the concentration of *2,3,5,6-tetrachloro-4-(methylsufonyl) pyridine in said mixture being sufficient to render a second thermoplastic composition resistant to microbiological degradation when said mixture is added to said second thermoplastic composition at a sufficiently low concentration to render said mixture and said second thermoplastic composition compatible.*

26. [The process of claim 25 wherein the resin of the microbiocidally active composition] *The process for forming a solid thermoplastic composition containing an effective concentration of a microbiocide but at a concentration less than that which presents a toxicological hazard which comprises mixing a particulate microbiocidally active composition consisting essentially of a homogeneous melt blended mixture of a first solid thermoplastic resin which* is polyvinyl chloride *and from 1 to 80 weight percent of a microbiocide based upon the weight of said first thermoplastic resin which is present in the mixture at a concentration of at least 20 times greater than the normal upper usage concentration of the microbiocide and wherein said microbiocide is immobilized and rendered physiologically inert in said first resin, with a second thermoplastic composition at a temperature above the softening temperature of the microbiocidally active composition and the second thermoplastic composition, the concentration of the microbiocidally active composition being sufficiently low to render it compatible with said second thermoplastic composition, and cooling the mixture to form a solid containing the microbiocidally active composition and second thermoplastic resin in homogeneous admixture.*

27. [The process of claim 25 wherein the resin of the microbiocidally active composition] *The process for forming a solid thermoplastic composition containing an effective concentration of a microbiocide but at a concentration less than that which presents a toxicological hazard which comprises mixing a particulate microbiocidally active composition consisting essentially of a homogeneous melt blended mixture of a first solid thermoplastic resin* which is a copolymer of vinyl chloride and vinyl acetate *and from 1 to 80 weight percent of a microbiocide based upon the weight of said first thermoplastic resin which is present in the mixture at a concentration of at least 20 times greater than the normal upper usage concentration of the microbiocide and wherein said microbiocide is immobilized and rendered physiologically inert in said first resin, with a second thermoplastic composition at a temperature above the softening temperature of the microbiocidally active composition and the second thermoplastic composition, the concentration of the microbiocidally active composition being sufficiently low to render it compatible with said second thermoplastic composition, and cooling the mixture to form a solid containing the microbiocidally active composition and second thermoplastic resin in homogeneous admixture.*

28. [The process of claim 25 wherein the microbiocide is] *The process for forming a solid thermoplastic composition containing an effective concentration of a microbiocide but at a concentration less than that which presents a toxicological hazard which comprises mixing a particulate microbiocidally active composition consisting essentially of a homogeneous melt blended mixture of a first solid thermoplastic resin and from 1 to 80 weight percent of* 10,10′-oxybisphenoxarsine *based upon the weight of said first thermoplastic resin which is present in the mixture of a concentration of at least 20 times greater than the normal upper usage concentration of* 10,10′-oxybisphenoxarsine *and wherein* 10,10′-oxybisphenoxarsine *is immobilized and rendered physiologically inert in said first resin, with a second thermoplastic composition at a temperature above the softening temperature of the microbiocidally active composition and the second thermoplastic composition, the concentration of the microbiocidally active composition being sufficiently low to render it compatible with said second thermoplastic composition, and cooling the mixture to form a solid containing the microbiocidally active composition and second thermoplastic resin in homogeneous admixture.*

30. [The process of claim 25 wherein the microbiocide is] *The process for forming a solid thermoplastic composition containing an effective concentration of a microbiocide but at a concentration less than that which presents a toxicological hazard which comprises mixing a particulate microbiocidally active composition consisting essentially of a homogeneous melt blended mixture of a first solid thermoplastic resin and from 1 to 80 weight percent of* N-(trichloromethylthio)-4-cyclohexene-1,2-dicarboxamide *based upon the weight of said first thermoplastic resin which is present in the mixture at a concentration of at least 20 times greater than the normal upper usage concentration of* N-(trichloromethylthio)-4-cyclohexene-1,2-dicarboxamide *and wherein* N-(trichloromethylthio)-4-cyclohexene-1,2-dicarboxamide *is immobilized and rendered physiologically inert in said first resin, with a second thermoplastic composition at a temperature above the softening temperature of the microbiocidally active composition and the second thermoplastic composition, the concentration of the microbiocidally active composition being sufficiently low to render it compatible with said second thermoplastic composition, and cooling the mixture to form a solid containing the microbiocidally active composition and second thermoplastic resin in homogeneous admixture.*

32. [The process of claim 25 wherein the microbiocide is] *The process for forming a solid thermoplastic composition containing an effective concentration of a microbiocide but at a concentration less than that which presents a toxicological hazard which comprises mixing a particulate microbiocidally active composition consisting essentially of a homogeneous melt blended mixture of a first solid thermoplastic resin and from 1 to 80 weight percent of* 2,3,5,6-tetrachloro-4-(methylsulfonyl) pyridine *based upon the weight of said first thermoplastic resin which is present in the mixture at a concentration of at least 20 times greater than the normal upper usage concentration of* 2,3,5,6-tetrachloro-4-(methylsulfonyl) pyridine *and wherein* 2,3,5,6-tetrachloro-4-(methylsulfonyl) pyridine *is immobilized and rendered physiologically inert in said first resin, with a second thermoplastic composition at a temperature above the softening temperature of the mi-* crobiocidally active composition and the second thermoplastic composition, the concentration of the microbiocidally active composition being sufficiently low to render it compatible with said second thermoplastic composition, and cooling the mixture to form a solid containing the microbiocidally active composition and second thermoplastic resin in homogeneous admixture.

34. [The process of claim 25 wherein the microbiocide is] *The process for forming a solid thermoplastic composition containing an effective concentration of a microbiocide but at a concentration less than that which presents a toxicological hazard which comprises mixing a particulate microbiocidally active composition consisting essentially of a homogeneous melt blended mixture of a first solid thermoplastic resin and from 1 to 80 weight percent of* N-(trichloromethylthio) phthalimide *based upon the weight of said first thermoplastic resin which is present in the mixture at a concentration of at least 20 times greater than the normal upper usage concentration of* N-(trichloromethylthio) phthalimide *and wherein* N-(trichloromethylthio) phthalimide *is immobilized and rendered physiologically inert in said first resin, with a second thermoplastic composition at a temperature above the softening temperature of the microbiocidally active composition and the second thermoplastic composition, the concentration of the microbiocidally active composition being sufficiently low to render it compatible with said second thermoplastic composition, and cooling the mixture to form a solid containing the microbiocidally active composition and second thermoplastic resin in homogeneous admixture.*

36. [The process of claim 25 wherein the microbiocide is] *The process for forming a solid thermoplastic composition containing an effective concentration of a microbiocide but at a concentration less than that which presents a toxicological hazard which comprises mixing a particulate microbiocidally active composition consisting essentially of a homogeneous melt blended mixture of a first solid thermoplastic resin and from 1 to 80 weight percent of* tributyl tin fluoride *based upon the weight of said first thermoplastic resin which is present in the mixture at a concentration of at least 20 times greater than the normal upper usage concentration of tributyl tin fluoride and wherein tributyl tin fluoride is immobilized and rendered physiologically inert in said first resin, with a second thermoplastic composition at a temperature above the softening temperature of the microbiocidally active composition and the second thermoplastic composition, the concentration of the microbiocidally active composition being sufficiently low to render it compatible with said second thermoplastic composition, and cooling the mixture to form a solid containing the microbiocidally active composition and second thermoplastic resin in homogeneous admixture.*

38. A thermoplastic resin composition resistant to microbiological degradation comprising between about 0.5 and 5.0 weight percent of a composition comprising vinyl chloride-vinyl acetate copolymer and between 1 to 80 weight percent of a [first] microbiocide at a concentration of at least 20 times greater than the normal upper usage concentration of the microbiocide wherein
said first composition is homogeneously dispersed in a second thermoplastic resin composition comprising a thermoplastic resin which is not a vinyl chloride-vinyl acetate copolymer.

39. [The composition of claim 38 wherein the microbiocide is] *A thermoplastic resin composition resistant to microbiological degradation comprising between about 0.5 and 5.0 weight percent of a composition comprising vinyl chloride-vinyl acetate copolymer and between 1 and 80 weight percent of* 10,10'-oxybisphenoxarsine *at a concentration of at least 20 times greater than the normal upper usage concentration of the microbiocide wherein said first composition is homogeneously dispersed in a second thermoplastic resin composition comprising a thermoplastic resin which is not a vinyl chloride-vinyl acetate copolymer.*

40. [The composition of claim 38 wherein the thermoplastic resin is] *A thermoplastic resin composition resistant to microbiological degradation comprising between about 0.5 and 5.0 weight percent of a composition comprising vinyl chloride-vinyl acetate copolymer and between 1 and 80 weight percent of a microbiocide at a concentration of at least 20 times greater than the normal upper usage concentration of the microbiocide wherein said first composition is homogeneously dispersed in a second thermoplastic resin composition comprising* [a thermoplastic resin which is not a vinyl chloride-vinyl acetate copolymer] a polyurethane.

41. [The composition of claim 38 wherein the thermoplastic resin is] *A thermoplastic resin composition resistant to microbiological degradation comprising between about 0.5 to 5.0 weight percent of a composition comprising vinyl chloride-vinyl acetate copolymer and between 1 and 80 weight percent of a microbiocide at a concentration of at least 20 times greater than the normal upper usage concentration of the microbiocide wherein said first composition is homogeneously dispersed in a second thermoplastic resin composition comprising* [a thermoplastic resin which is not a vinyl chloride-vinyl acetate copolymer] a polyethylene.

42. [The composition of claim 38 wherein the thermoplastic resin is] *A thermoplastic resin composition resistant to microbiological degradation comprising between about 0.5 and 5.0 weight percent of a composition comprising vinyl chloride-vinyl acetate copolymer and between 1 and 80 weight percent of a microbiocide at a concentration of at least 20 times greater than the normal upper usage concentration of the microbiocide wherein said first composition is homogeneously dispersed in a second thermoplastic resin composition comprising* [a thermoplastic resin which is not a vinyl chloride-vinyl acetate copolymer] polyvinyl chloride.

43. *A solid composition consisting essentially of a homogeneous melt blended mixture of a solid thermoplastic polyamide resin and from 1 to 80 weight percent of a microbiocide based upon the weight of said solid composition which is present in the mixture at a concentration of at least about 20 times greater than the normal upper usage concentration of the microbiocide and wherein said microbiocide is immobilized and rendered physiologically inert in said resin, the concentration of said microbiocide in said mixture being sufficient to render a second thermoplastic composition resistant to microbiological degradation when said mixture is added to said second thermoplastic composition at a sufficiently low concentration to render said mixture and said second thermoplastic composition compatible.*

44. *A solid composition consisting essentially of a homogeneous melt blended mixture in particulate form of a solid thermoplastic polyamide resin and from 1 to 80 weight percent of a microbiocide based upon the weight of said solid composition which is present in the mixture at a concentration of at least about 20 times greater than the normal upper usage concentration of the microbiocide and wherein said microbiocide is immobilized and rendered*

*physiologically inert in said resin, the concentration of said microbiocide in said mixture being sufficient to render a second thermoplastic composition resistant to microbiological degradation when said mixture is added to said second thermoplastic composition at a sufficiently low concentration to render said mixture and said second thermoplastic composition compatible.*

*45. A solid composition consisting essentially of a homogeneous melt blended mixture in particulate form of a solid thermoplastic polyamide resin and from 1 to 80 percent of 10,10'-oxybisphenoxarsine based upon the weight of said solid composition which is present in the mixture at a concentration of at least about 20 times greater than the normal upper usage concentration of 10,10'-oxybisphenoxarsine and wherein 10,10'-oxybisphenoxarsine is immobilized and rendered physiologically inert in said resin, the concentration of 10,10'-oxybisphenoxarsine in said mixture being sufficient to render a second thermoplastic composition resistant to microbiological degradation when said mixture is added to said second thermoplastic composition at a sufficiently low concentration to render said mixture and said second thermoplastic composition compatible.*

*46. A solid composition consisting essentially of a homogeneous melt blended mixture of a solid thermoplastic polystyrene resin and from 1 to 80 weight percent of a microbiocide based upon the weight of said solid composition which is present in the mixture at a concentration of at least about 20 times greater than the normal upper usage concentration of the microbiocide and wherein said microbiocide is immobilized and rendered physiologically inert in said resin, the concentration of said microbiocide in said mixture being sufficient to render a second thermoplastic composition resistant to microbiological degradation when said mixture is added to said second thermoplastic composition at a sufficiently low concentration to render said mixture and said second thermoplastic composition compatible.*

*47. A solid composition consisting essentially of a homogeneous melt blended mixture in particulate form of a solid thermoplastic polystyrene resin and from 1 to 80 weight percent of a microbiocide based upon the weight of said solid composition which is present in the mixture at a concentration of at least about 20 times greater than the normal upper usage concentration of the microbiocide and wherein said microbiocide is immobilized and rendered physiologically inert in said resin, the concentration of said microbiocide in said mixture being sufficient to render a second thermoplastic composition resistant to microbiological degradation when said mixture is added to said second thermoplastic composition at a sufficiently low concentration to render said mixture and said second thermoplastic composition compatible.*

*48. A solid composition consisting essentially of a homogeneous melt blended mixture in particulate form of a solid thermoplastic polystyrene resin and from 1 to 80 weight percent of 10,10'-oxybisphenoxarsine based upon the weight of said solid composition which is present in the mixture at a concentration of at least about 20 times greater than the normal upper usage concentration of 10,10'-oxybisphenoxarsine and wherein 10,10'-oxybisphenoxarsine is immobilized and rendered physiologically inert in said resin, the concentration of 10,10'-oxybisphenoxarsine in said mixture being sufficient to render a second thermoplastic composition resistant to microbiological degradation when said mixture is added to said second thermoplastic composition at a sufficiently low concentration to render said mixture and said second thermoplastic composition compatible.*

*49. A solid composition consisting essentially of a homogeneous melt blended mixture of a solid thermoplastic resin which is a polyolefin homopolymer and from 1 to 80 weight percent of a microbiocide based upon the weight of said solid composition which is present in the mixture at a concentration of at least about 20 times greater than the normal upper usage concentration of the microbiocide and wherein said microbiocide is immobilized and rendered physiologically inert in said resin, the concentration of said microbiocide in said mixture being sufficient to render a second thermoplastic composition resistant to microbiological degradation when said mixture is added to said second thermoplastic composition at a sufficiently low concentration to render said mixture and said second thermoplastic composition compatible.*

*50. A solid composition consisting essentially of a homogeneous melt blended mixture in particulate form of a solid thermoplastic resin which is a polyolefin homopolymer and from 1 to 80 weight percent of a microbiocide based upon the weight of said solid composition which is present in the mixture at a concentration of at least about 20 times greater than the normal upper usage concentration of the microbiocide and wherein said microbiocide is immobilized and rendered physiologically inert in said resin, the concentration of said microbiocide in said mixture being sufficient to render a second thermoplastic composition resistant to microbiological degradation when said mixture is added to said second thermoplastic composition at a sufficiently low concentration to render said mixture and said second thermoplastic composition compatible.*

*51. A solid composition consisting essentially of a homogeneous melt blended mixture in particulate form of a solid thermoplastic resin which is a polyolefin homopolymer and from 1 to 80 weight percent of 10,10'-oxybisphenoxarsine based upon the weight of said solid composition which is present in the mixture at a concentration of at least about 20 times greater than the normal upper usage concentration of 10,10'-oxybisphenoxarsine and wherein 10,10'-oxybisphenoxarsine is immobilized and rendered physiologically inert in said resin, the concentration of 10,10'-oxybisphenoxarsine in said mixture being sufficient to render a second thermoplastic composition resistant to microbiological degradation when said mixture is added to said second thermoplastic composition at a sufficiently low concentration to render said mixture and said second thermoplastic composition compatible.*

*52. The process for forming a solid thermoplastic composition containing an effective concentration of a microbiocide but at a concentration less than that which presents a toxicological hazard which comprises mixing a particulate microbiocidally active composition consisting essentially of a homogeneous melt blended mixture of a first solid thermoplastic resin which is a copolymer of polyvinyl chloride and polyvinyl acetate and from 1 to 80 weight percent of 10,10'-oxybisphenoxarsine based upon the weight of said first thermoplastic resin which is present in the mixture at a concentration of at least 20 times greater than the normal upper usage concentration of 10,10'-oxybisphenoxarsine and wherein 10,10'-oxybisphenoxarsine is immobilized and rendered physiologically inert in said first resin, with a second thermoplastic composition at a temperature above the softening temperature of the microbiocidally active composition and the second thermoplastic composition, the concentration of the microbiocidally active composition being sufficiently low to render it compatible with said second thermoplastic composition, and cooling the mixture to form a solid containing the microbiocidally active composition and second thermoplastic resin in homogeneous admixture.*

* * * * *